United States Patent [19]
Anderson et al.

[11] Patent Number: 5,816,248
[45] Date of Patent: Oct. 6, 1998

[54] CHANNELED VAGINAL INSERT AND METHOD FOR TREATING UROGENITAL DISORDERS

[75] Inventors: David W. Anderson, Maple Grove; Robert E. Buuck, Bloomington; Arnold W. Thornton, Roseville; Xiao Kang Zhang, Champlin, all of Minn.

[73] Assignee: Iotek, Inc., Minneapolis, Minn.

[21] Appl. No.: 625,807

[22] Filed: Mar. 29, 1996

[51] Int. Cl.⁶ .................................................. A61F 6/06
[52] U.S. Cl. ............................................ 128/830; 128/832
[58] Field of Search ...................... 128/830–841

[56] References Cited

U.S. PATENT DOCUMENTS

| | | |
|---|---|---|
| 4,014,987 | 3/1977 | Heller ....................................... 128/832 |
| 4,034,756 | 7/1977 | Higuchi .................................... 128/832 |
| 4,217,898 | 8/1980 | Theeuwes . |
| 4,235,236 | 11/1980 | Theeuwes . |
| 4,237,888 | 12/1980 | Roseman et al. . |
| 4,250,611 | 2/1981 | Wong . |
| 4,286,587 | 9/1981 | Wong . |
| 4,286,596 | 9/1981 | Rubinstein . |
| 4,291,014 | 9/1981 | Keith et al. . |
| 4,304,232 | 12/1981 | Michaels . |
| 4,312,347 | 1/1982 | Magoon et al. . |
| 4,402,693 | 9/1983 | Roseman et al. . |
| 4,402,695 | 9/1983 | Wong . |
| 4,411,658 | 10/1983 | Godbille et al. . |
| 4,438,139 | 3/1984 | Keith et al. . |
| 4,439,196 | 3/1984 | Higuchi . |
| 4,449,980 | 5/1984 | Millar et al. . |
| 4,469,671 | 9/1984 | Zimmerman et al. . |
| 4,553,965 | 11/1985 | Conn et al. . |
| 4,564,362 | 1/1986 | Burnhill . |
| 4,578,076 | 3/1986 | Luukkainen ............................ 128/833 |
| 4,582,052 | 4/1986 | Dunn et al. . |
| 4,585,451 | 4/1986 | Millar . |
| 4,596,576 | 6/1986 | de Nijs . |
| 4,601,714 | 7/1986 | Burnhill . |
| 4,629,449 | 12/1986 | Wong . |
| 4,770,167 | 9/1988 | Kaali ....................................... 128/832 |
| 4,804,380 | 2/1989 | Lassen et al. . |
| 4,822,616 | 4/1989 | Zimmerman et al. . |
| 4,846,824 | 7/1989 | Lassen et al. . |
| 4,871,543 | 10/1989 | Lindskog et al. . |
| 4,881,526 | 11/1989 | Johnson et al. . |
| 4,961,931 | 10/1990 | Wong . |
| 5,007,894 | 4/1991 | Enhorning . |
| 5,019,372 | 5/1991 | Folkman et al. . |
| 5,036,867 | 8/1991 | Biswas . |
| 5,045,079 | 9/1991 | West . |
| 5,188,122 | 2/1993 | Phipps et al. . |
| 5,190,766 | 3/1993 | Ishihara . |
| 5,299,581 | 4/1994 | Donnell et al. . |
| 5,386,836 | 2/1995 | Biswas . |
| 5,458,568 | 10/1995 | Racchini et al. . |
| 5,499,971 | 3/1996 | Shapland et al. . |

*Primary Examiner*—Michael A. Brown
*Attorney, Agent, or Firm*—Merchant, Gould, Smith, Edell, Welter & Schmidt, P.A.

[57] ABSTRACT

A vaginal insert for delivering an agent to a urogenital tract in a patient. The patient has a vagina, and the vagina has an anterior wall. The vaginal insert comprises a member sized to fit within the vagina. The member has a surface defining a channel configured to engage the anterior vaginal wall and receive tissue proximal to the urethra. The member defines a chamber for retaining a supply of the agent and a plurality of delivery ports. At least some of the delivery ports are located along the channel. The plurality of delivery ports are in fluid communication with the chamber. The vaginal insert also comprises first and second electrodes. The first electrode is operably connected to the member. The first and second electrodes configured to be operably connected to a power source so that an electrical current can pass between the first and second electrodes and through tissue proximal the urethra.

22 Claims, 6 Drawing Sheets

FIG. 11B

CHANNELED VAGINAL INSERT AND METHOD FOR TREATING UROGENITAL DISORDERS

TECHNICAL FIELD

The present invention relates to the treatment of urogenital disorders and more particularly to a channeled vaginal insert and method for delivering an agent to the urogenital tract.

BACKGROUND

Urinary incontinence is an involuntary discharge of urine from the bladder. Incontinence can be caused by a variety of factors including pregnancy, estrogen deficiency, general weakening of the spectral pelvic floor muscles, surgery along the urinary tract, infection, and other maladies localized in the urinary tract. In addition to incontinence, women can experience chronic pain and infections along the urinary tract. These conditions are widespread and affect millions of people.

There are several types of incontinence, including stress incontinence, urge incontinence, and total incontinence. Stress incontinence occurs when a person's body is under physical stress. People suffering from this type of incontinence might experience urine discharge during physically stressful events. Examples of stressful events include coughing, laughing, and rigorous exercise.

Urge incontinence is characterized as an urgent desire to urinate and results in total discharge of the bladder. During urge incontinence, the detrusor muscle contracts or spasms inappropriately as the bladder fills. Such a contraction can occur suddenly, without warning, and is frequently accompanied by a strong desire to void the bladder. Unstable bladder activity caused by urge incontinence is a common type of incontinence in females. This type of incontinence can occur at any time, but frequently occurs when a person has a sudden change in their physical position. Total incontinence is characterized by a total lack of control over urine discharge and is frequently caused by complete failure of the sphincter muscles.

For practical purposes, treatments for an unstable bladder are divided into simple and complex therapy. Simply therapy includes behavioral modification and drug therapy, while complex therapy encompasses electrical stimulation and radical surgery, which is performed either to denervate the bladder or to augment its capacity.

When treating detrusor instability, the use of therapeutic agents such as drugs represents a pharmacologic attempt to interfere with bladder smooth muscle contraction. Various agents may work at several different points in the physiologic pathway leading to detrusor contraction. Possible sites of action include modulating control mechanisms in the central nervous system, blocking the activity of acetylcholine (which is the major neurotransmitter in the bladder), directly relaxing bladder smooth muscle, or regulating other substances believed to have a modulating effect on bladder contractile function. Agents that are useful in treating detrusor instability may be broken down into at least six categories: anticholinergic drugs, antispasmodic or spasmolytic drugs, tricyclic antidepressants, calcium channel blockers, prostaglandin synthetase inhibitors, and estrogens.

Because the main neuroreceptor involved in bladder contraction is acetylcholine, most agents used in treating detrusor instability/hyperreflexia are drugs having significant anticholinergic properties, even if these properties are not the main mechanism of action when the drugs are categorized pharmacologically. The prototypical anticholinergic drug is atropine, a powerful belladonna alkaloid that exerts its effects through competitive antimuscarinic activity at parasympathetic neuroreceptor junctions. These effects are felt in many organ systems, including the bladder.

Because these receptors are found in many parts of the body, the use of any anticholinergic drug will produce effects on many physiologic parameters, not just those related to bladder function. Atropine is far more potent than any of the drugs used in the treatment of detrusor over activity. However, there has been little progress in developing anticholinergic drugs that act specifically on the bladder. As a result, the side effect patterns of these other drugs will follow roughly the same dose-response pattern as atropine.

The most common side effects that may be experienced include a dry mouth due to suppression of salivary and oropharyngeal secretions, occasional drowsiness, constipation due to decreased gastrointestinal motility, increased heart rate due to vagal blockade, and transient blurring of vision due to blockade of the sphincter of the iris and the ciliary muscle of the lens of the eye. Delivering agents to treat disorders other than detrusor instability can also cause serious side effects or harm to the patient.

Therefore, there is a need in the art for methods and apparatuses for treating various maladies that effect the urinary tract. There is also a need for methods and apparatuses for delivering an agent to tissue proximal to the urinary tract while minimizing exposure of the agent to other tissue.

SUMMARY

The present invention is directed to a vaginal insert for delivering an agent to a urogenital tract in a patient. The patient has a vagina, and the vagina has an anterior wall. The vaginal insert comprises a base member sized to fit within the vagina. An agent-retaining member is operatively connected to the base member. The agent-retaining member has an outer surface. The outer surface defines a channel configured to engage the anterior vaginal wall and receive tissue proximal to the urethra.

The present invention is also directed to a method of delivering an agent to a urogenital tract within a patient. The method comprises the steps of: inserting a vaginal insert into the vagina, the vaginal insert defining a channel and containing an agent, the channel being sized to engage the anterior vaginal wall and receive tissues proximal the urinary tract; positioning tissue proximal to the urinary tract into the channel; and transporting the agent from the vaginal insert to tissue proximal the urinary tract.

DETAILED DESCRIPTION

The invention initially will be described in general terms in conjunction with a brief description of the female anatomy. Various vaginal inserts and methods then will be described in detail with reference to the drawings, wherein like reference numbers represent like parts and assemblies throughout the several views. Reference to the preferred embodiment does not limit the scope of the invention, which is limited only by the scope of the claims attached hereto.

Figure 1:
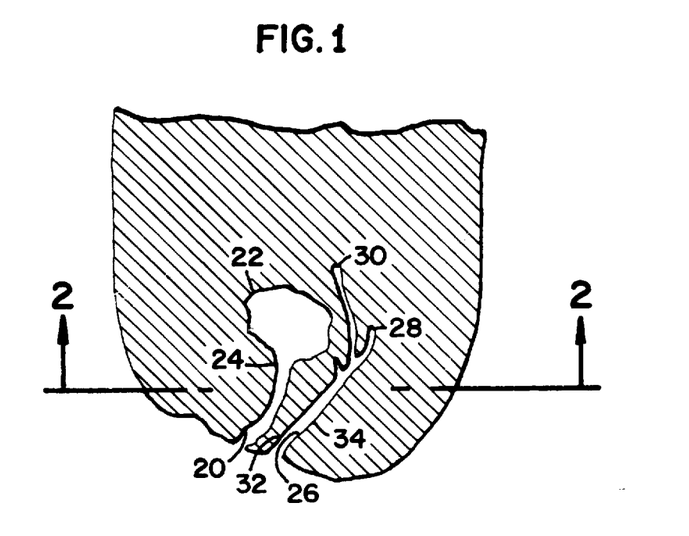
FIG. 1 shows a vertical cross-section of the female genital and urinary anatomy.
Figure 2:
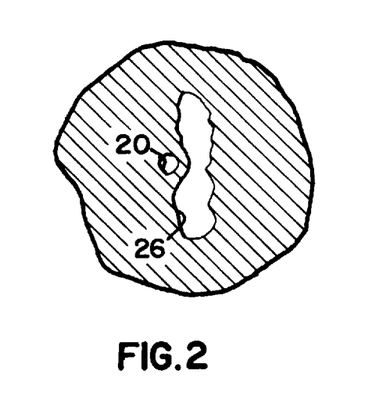
FIG. 2 shows a horizontal cross-section taken along line 2—2 of the female genital and urinary anatomy shown in FIG. 1.

Referring to FIG. 1, the female body defines a urethra 20, which provides a discharge lumen that is in fluid communication with a bladder 22. The urethra 20 meets the bladder 22 at the bladder neck 24. The urethra 20, bladder 22, and bladder neck 24 are all parts of the urinary tract. Additionally, a vagina 26 is located directly behind the urethra 20 and leads to the cervix 28 and the uterus 30. The vagina has anterior and posterior walls 32 and 34 respectively. Only a thin layer of tissue is located between the urethra 20 and the anterior vaginal wall 32.

The present invention generally relates to an apparatus and method of inserting an agent into the vagina 26 and transporting that agent from the vagina 26, through the anterior vaginal wall 32, and to the tissue surrounding the urinary tract. The target tissue surrounding the urinary tract can be the bladder 22, the neck 24 of the bladder 22, or the urethra 20. The techniques for transporting the agent from the vagina 26 to the tissue surrounding the urinary tract can involve passive or active delivery. Although the following description discusses delivering the agent to the urinary tract, the present invention can be used to deliver the agent to any tissue within the urogenital tract.

Examples of passive delivery include natural absorption. Examples of active delivery include iontophoresis; phonophoresis; and magnetophoresis, which involves magnetic activation of the agent.

Additionally, the invention can be used to deliver agents for treating a variety of maladies such as incontinence; muscle spasms that have undesirable results such as involuntary bladder contractions; urethral syndrome; interstitial cystitis; and general maladies such as pain, infections, and diseased tissue. Various agents can be used to treat these maladies including, but not limited to, anticholinergic drugs such as atropine and ditropan, α-adrenergic agents, antispasmodic or spasmolytic drugs, tricyclic antidepressants, calcium channel blockers, prostaglandin synthetase inhibitors, estrogens, and other agents that act on skeletomuscles.

The present invention has many advantages. One advantage is that the agent is delivered directly to the tissue surrounding the urinary tract. Exposure of the agent to other parts of the body, including the reproductive organs, is diminished. As a result, the risk of side effects is minimized. This advantage is very important when delivering toxic drugs or hormones that can cause cancer, especially when delivery occurs on a periodic or frequent basis.

Minimizing the amount of agent that is delivered outside of the urinary tract also reduces waste. Thus, a smaller dose of the agent can be used with the present invention while increasing its effectiveness. In other words, the agent that is delivered into the patient will be used much more efficiently.

Figure 3:
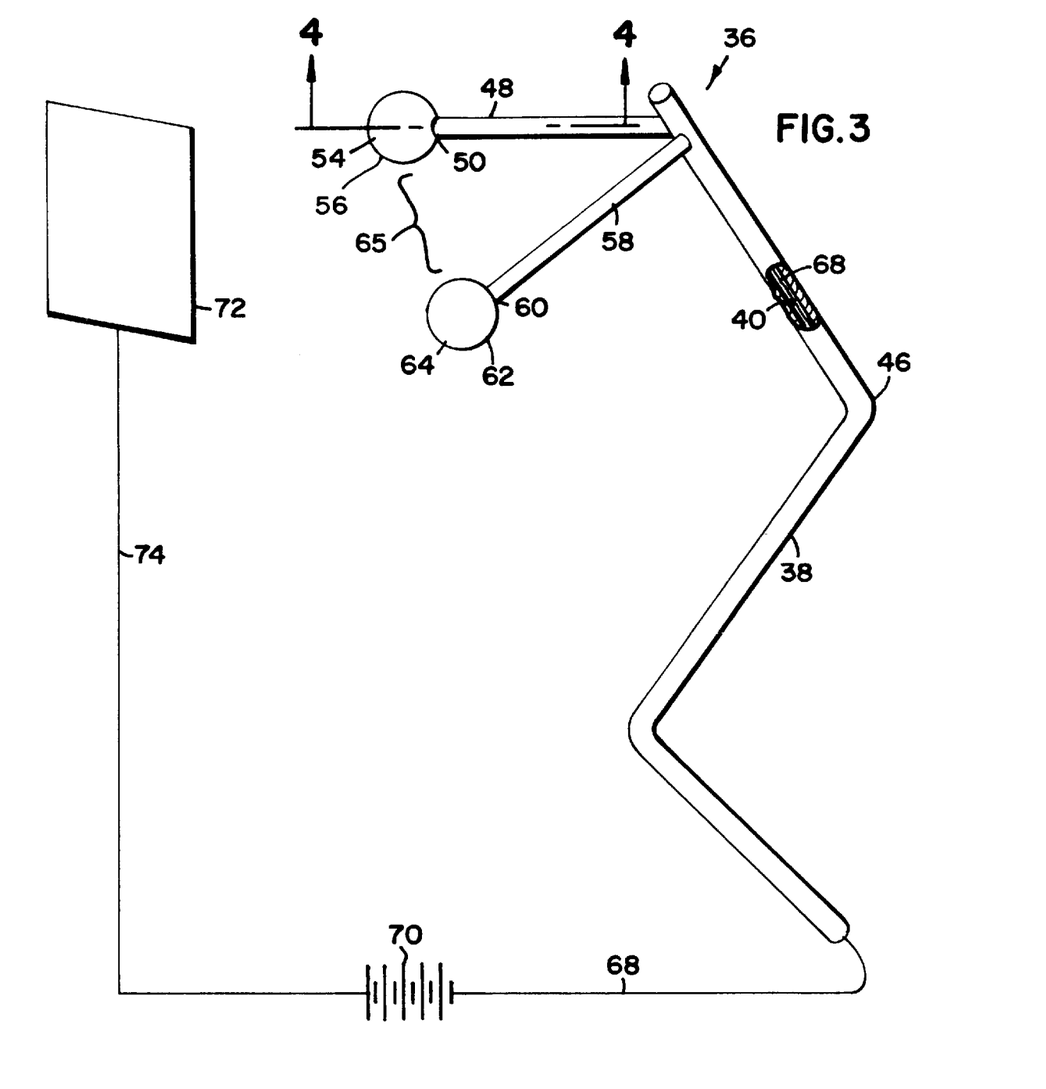
FIG. 3 shows a perspective view of a vaginal insert used to deliver an agent to the urogenital tract.
Figure 4:
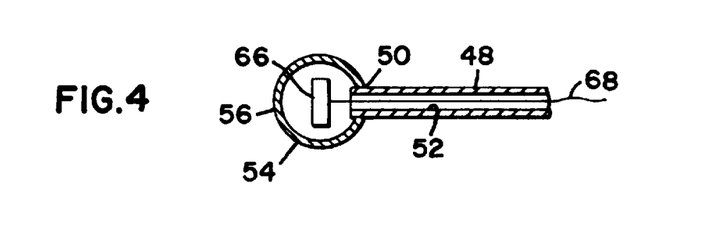
FIG. 4 shows a partial cross-section of the device shown in FIG. 3, the partial cross-section taken along line 4—4.

FIGS. 3 and 4 illustrate a vaginal insert, generally shown as 36, that has a main body or portion 38. The main body 38 is elongated and defines a main lumen 40. Additionally, the main body 38 is bent at an intermediate section 46.

A first member or portion 48 is operably connected to, and projects outward from the main body 38. The first projecting member 48 has a projecting end 50 and defines a first branch lumen 52 that is in fluid communication with a first balloon 54. The first balloon 54 is operably connected to the projecting end 50 and is formed from a porous membrane 56.

A second projecting member or portion 58 is substantially similar to the first member 48. Specifically, the second member 58 is operably connected to the main body 38, has a projecting end 60, and defines a second branch lumen (not shown). Additionally, a second balloon 62 is formed from a porous membrane 64 and is operably connected to the projecting end 60. The second balloon 62 is in fluid communication with the second branch lumen.

First and second projecting members 48 and 58 are positioned so that they form a gap or opening 65 therebetween. The gap 65 is sized to receive the bladder neck 24 when the first and second projecting members 48 and 58 engage the anterior vaginal wall 32. Additionally, the first and second projecting members 48 and 58 are positioned so that when they engage the anterior vaginal wall 32, the intermediate section 46 of the main body 38 engages the posterior vaginal wall 34.

A first electrode 66 is positioned within the first balloon 54. The first electrode 66 is connected to a first lead 68 that extends through the first branch lumen 52 and the main lumen 40. The first lead 68 is then connected to a power source 70. In one embodiment, a second electrode 72 is remotely located and is connected to the power supply 70 by a second lead 74. In this configuration, the second electrode 72 is a patch-type electrode that can be placed against the patient's skin. A third electrode (not shown) is substantially similar to the first electrode 66 and is located within the second balloon 62. A third lead (not shown) connects the third electrode to the first lead 68 so that the first 66 and third electrodes have the same polarity.

The power supply 70 can be a simple DC power source that provides a direct current between the first and third electrodes and the second electrode. Alternatively, the power supply 70 can provide a current having a predetermined type of waveform. Additionally, the power supply can provide an electric current at intermittent intervals.

In use, the vaginal insert 36 is placed within the vagina 26 and oriented so that the first and second balloons 54 and 62 engage and press into the anterior vaginal wall 20 so that the bladder neck 24 is positioned within the gap 65. In this position, the intermediate section engages the posterior vaginal wall 34 providing frictional engagement to secure the vaginal insert 36 in a stationary position. One skilled in the art will realize that the first and second balloons 54 and 62 can be positioned along other portions of the urinary tract such as the urethra 20.

After the vaginal insert 36 is secured in position, a fluid containing an agent is injected into the main lumen 40 so that the fluid flows through the first 52 and second branch lumens and inflates the first and second balloons 54 and 62. The second electrode 72 is placed against the patient's body at a position such as the patient's abdomen or thigh. The power supply 70 is then activated, which causes a current to flow between the first 66 and third electrodes and the second electrode 72. Electrons that form the current will flow from the first 66 and third electrodes, through the anterior vaginal wall 32, through the tissue proximate to the bladder neck 24, and to the second electrode 72. The electrons carry the agent from the first and second balloons 54 and 62 to the tissue proximate to the bladder neck 24.

One skilled in the art will realize that the vaginal insert 36 shown in FIG. 3 can have many alternative embodiments. For example, the first and second balloons 54 and 62 can be replaced with hollow spheres (not shown) that define a plurality of delivery ports. In this embodiment, the spheres may be covered with a porous membrane (not shown) to diffuse the current and prevent a hot spot at tissue that is adjacent to the delivery ports.

In another alternative embodiment, the first and second balloons 54 and 62 can be replaced with solid spheres (not shown) that have surface mounted electrodes (not shown) and are covered with a material (not shown) that can be impregnated with and release the agent. The material might be configured to naturally release the agent or to release the agent only if subjected to some type of active delivery mechanism such as iontophoresis or phonophoresis. Examples of suitable materials include a polymer matrix such as a hydrogel, a foam such as an open cell foam or a hydrophilic foam, and or any other material that can contain and release the agent.

In yet another alternative embodiment, the main body 38 defines first and second main lumens (not shown). The first main lumen is in fluid communication with the first balloon 54 via the first branch lumen 52. The second main lumen is in fluid communication with the second balloon 62 via the second branch lumen (not shown). In this embodiment, the first electrode 66 is positioned in the first balloon 54 and the second electrode 70 positioned in the second balloon 62. The first lead 68 extends through the first branch lumen 52 and the first main lumen. The second lead 74 extends through the second branch lumen and the second main lumen. Finally, the first and second leads 68 and 74 are connected to the power supply 70 in a manner that creates a bipolar electrode configuration.

An advantage of this design is that two agents can be simultaneously delivered. The first fluid having an agent and charged ions of one polarity are injected into the first balloon 54 and a second fluid containing an agent and ions of an opposite polarity are injected into the second balloon 62. As a result, two different agents can be simultaneously delivered, which can minimize the overall length of time required to deliver the prescribed dose of agents.

Additionally, the same agent can be delivered from both the first and second balloons 54 and 62 using a bipolar configuration. Delivery in this manner is accomplished by linking the agent that is injected into the first balloon 54 to ions having one polarity and the agent that is injected into the second balloon 62 to ions having an opposite polarity. An advantage of this type of delivery is that the current density can be decreased, while still delivering the agent in an acceptable amount of time. Reducing the current density will help to alleviate the discomfort experienced by the patient. An alternative advantage is that delivery can be performed twice as fast, thereby minimizing the length of time the patient is in discomfort.

Figure 5:
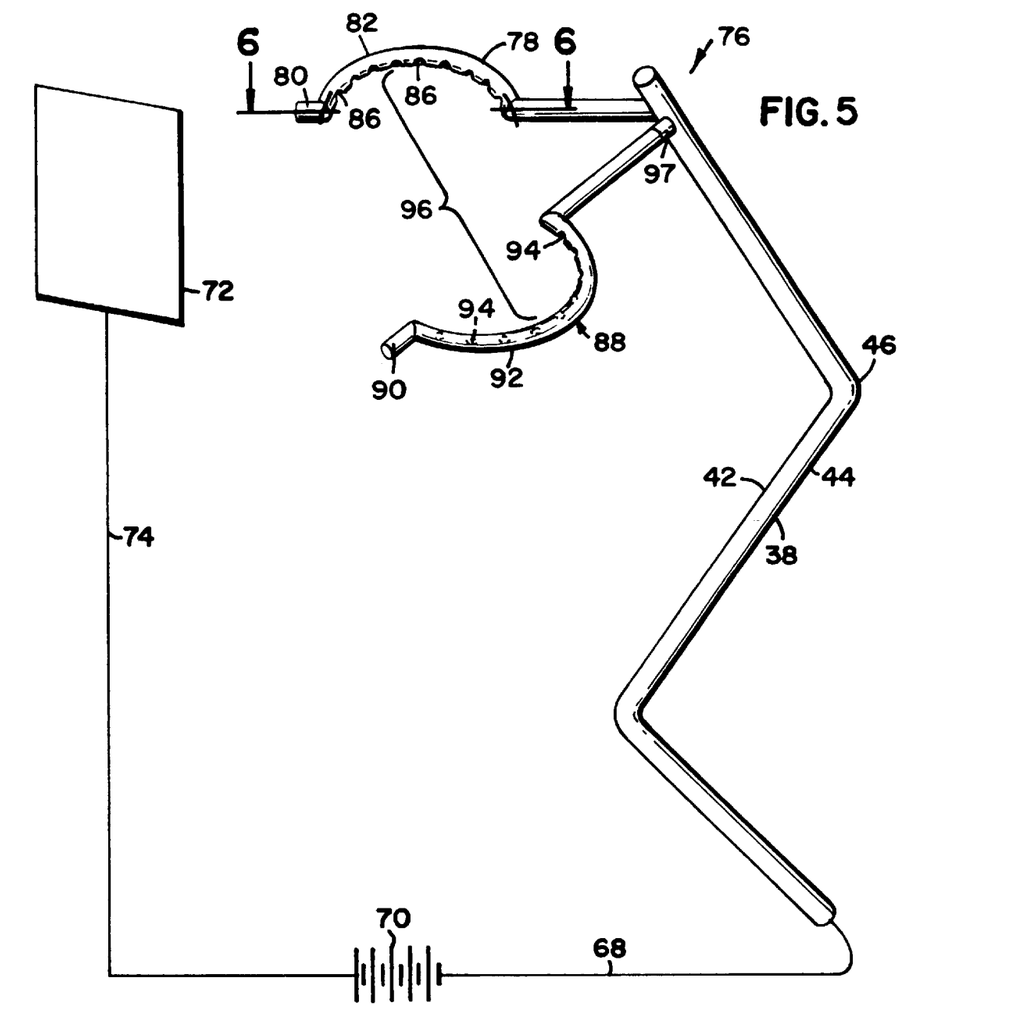
FIG. 5 shows an alternative embodiment of the vaginal insert used to deliver an agent to the urogenital tract.

FIG. 5 illustrates an alternative vaginal insert, generally shown as 76, in which a first member or portion 78 is operably connected to the main portion 38, has a projecting end 80, and has a curved segment 82 that is shaped to conform to the bladder neck 24. The curved segment 82 can have a C-shaped configuration. Additionally, the first projecting member 78 defines a first branch lumen 84 that is in fluid communication with the main lumen 40. Delivery ports 86 are defined in the curved segment 82 and are in fluid communication with the first branch lumen 84.

The second projecting member 88 is substantially similar to the first projecting member 78 and has a projecting end 90, a curved segment 92, a second branch lumen (not shown) that is in fluid communication with the main lumen 40, and delivery ports 94 that are in fluid communication with the second branch lumen. Additionally, the second projecting member 88 has a flexible segment 97 that allows the first and second projecting members 78 and 88 to move between an open state and a closed state.

When in a closed state, the projecting ends 80 and 90 of the first and second projecting members 78 and 88 are adjacent to one another. In the closed state, the curved segments 82 and 92 form a gap or opening 96 that is sized to allow the bladder neck and proximal tissue to pass therethrough. When in the open state, the opening 96 is configured to receive the bladder neck 24 and proximal tissue.

Figure 6:
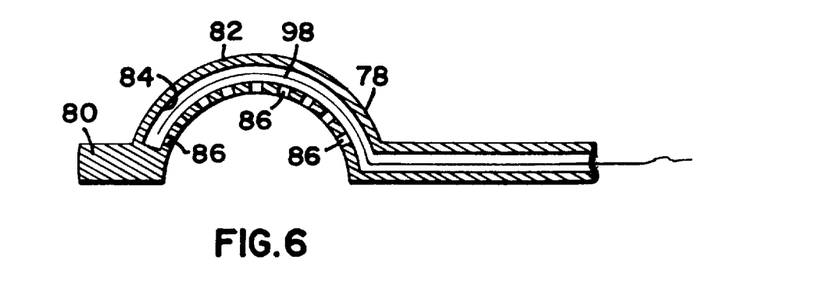
FIG. 6 shows a partial cross-section of the device shown in FIG. 5, the partial cross-section taken along line 6—6.

Referring to FIG. 6, a first electrode 98 is positioned in the first branch lumen 84 and is connected to the first lead 68 that extends through the main lumen 40. The second electrode 72 is remotely located and connected to the second lead 74. A third electrode (not shown) is positioned in the second branch lumen and is also connected to the first lead 68. The power supply 70 is connected to the first and second leads 68 and 74 so that the polarity of the first 98 and third electrodes is opposite to the polarity of the second electrode 72.

In use, the vaginal insert 76 is inserted into the vagina 26 so that the first and second projecting members 78 and 88 are in the open state and engage the anterior vaginal wall 32, thereby projecting along opposite sides of the bladder neck 24. The first and second projecting members 78 and 88 are then shifted to the closed state so that the delivery ports 86 and 94 substantially circumscribe the bladder neck 24. Fluid is then injected through the main lumen 40 so that it seeps through the delivery ports 86 and 94. Simultaneously, current is passed between the first 98 and third electrodes and the second electrode 72. The iontophoretic current helps to transport the fluid through the tissue of the anterior vaginal wall 32 and to the tissue proximal to the bladder neck 24. If the vaginal insert 76 has a bipolar configuration, fluids containing agents with oppositely charged ions can be injected into the first 84 and second branch lumens, respectively.

Similar to the embodiment shown in FIG. 3, one skilled in the art will realize that the vaginal insert 76 also can be configured to have a bipolar configuration in which the first electrode 98 having one polarity is positioned in the first branch lumen and the second electrode 72 having an opposite polarity is positioned in the second branch lumen. The main body 38 has first and second main lumens (not shown). The first lead 68 extends through the first main lumen and the second lead 74 extends through the second main lumen.

Additionally, the first and second projecting members 78 and 88 can be covered with a polymer matrix to help diffuse the current density and prevent hot spots at tissue adjacent to the delivery ports 86 and 94. One skilled in the art will also realize that the first and second projecting members 78 and 88 can be formed from a solid material; can have surface mounted electrodes; and can be coated with a material such as polymer matrix, hydrogel, or foam that is impregnated with an agent. Alternatively, the first and second projecting members 78 and 88 can be formed from the agent-retaining material itself.

Figure 7:
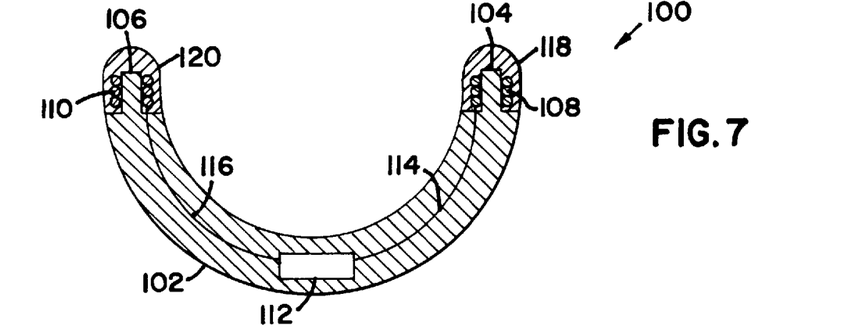
FIG. 7 shows a cross-section of an alternative embodiment of the vaginal insert used to deliver an agent to the urogenital tract.

FIG. 7 illustrates yet another alternative embodiment. In this embodiment, a vaginal insert, generally shown as 100, has a U-shape and defines a main portion 102 that is central between first and second portions 104 and 106. First and second portions 104 and 106 have a circumference that is smaller than the circumference of the main portion 102. Additionally, a first electrode 108 is wound around the first portion 104 and a second electrode 110 is wound around the second portion 106. The first and second electrodes 108 and 110 are connected to a power supply 112 via first and second leads 114 and 116.

The first portion 104 and first electrode 108 are covered by a first cap 118 formed from an absorbent material such as a polymer matrix, a hydrogel, or a foam. Any of these substances can be impregnated with an agent. The second portion 106 and second electrode 110 are similarly covered with an absorbent material that can be impregnated with an agent.

One skilled in the art will realize that the power supply 112 can have several possible configurations. In one configuration, the power supply 112 can be a battery that provides a simple direct current. In this situation, the patient would activate the power supply 112 before the vaginal insert 100 is placed in the vagina 26. In an alternative embodiment, the power supply 70 contains an inductive coil, similar to that of a transformer. In this embodiment, the vaginal insert 100 is positioned within the vagina 26 and the patient or caregiver can place a magnetic source against the body and proximal to the power supply 70. The magnetic source will generate a field that induces an electrical current in the magnetic coil.

In yet another embodiment, the inductive circuit is a resonant circuit that is tuned to a frequency in the radio frequency (RF) range (i.e., greater than about 9 KHz). In this embodiment, the resident circuit induces an electrical current when subject to a magnetic field that is oscillating at the resident frequency. One skilled in the art will realize that the power supply 112 can include an AC/DC converter so that a direct current is passed between the first and second electrodes 108 and 110. Alternatively, the power supply 112 can include additional circuitry to generate a current having a particular waveform. An advantage of using a resonant circuit is that interference from stray magnetic fields is minimized.

In use, the first cap 118 is impregnated with an agent having a pre-determined polarity. Additionally, the second cap 120 can be impregnated with an agent having an opposite polarity. The vaginal insert 100 is positioned within the vagina 26 so that the first and second portions 104 and 106 engage the anterior vaginal wall 32 and are positioned along opposite sides of the urinary tract. The main portion then engages the posterior vaginal wall 34, thereby securing the vaginal insert 100 in a stationary position. One skilled in the art will realize that the vaginal insert 100 can be positioned proximal to any portion of the urinary tract such as the bladder neck 24 or the urethra 20. The electric current then passes between the first and second electrodes 108 and 110 and transports the agent from the first and second caps 118 and 120 to tissue proximal to the urinary tract that is located and between the first and second portion 104 and 106.

Figure 8:
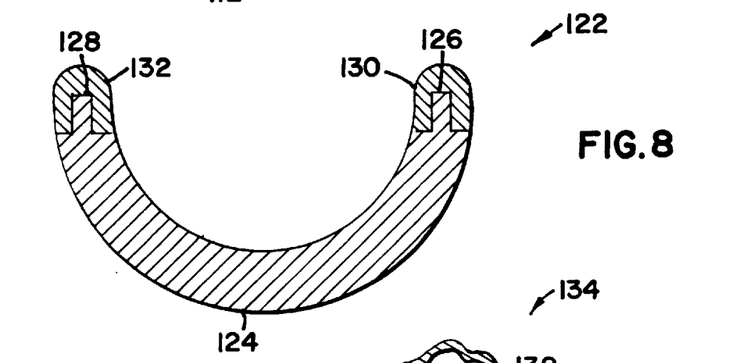
FIG. 8 shows a cross-section of another alternative embodiment of the device used to deliver an agent to the urogenital tract.

FIG. 8 illustrates another alternative embodiment that has a configuration substantially similar to the vaginal insert 100 and uses magnetophoresis to transport the agent. In particular, the vaginal insert, generally shown as 122, has a main portion 124, a first portion 126, and a second portion 128. First and second caps 130 and 132 formed of an agent-retaining material such as a polymer matrix cover the first and second portions 126 and 128, respectively. The first and second caps 130 and 132 are impregnated with magnetic particles in addition to an agent. In use, the vaginal insert 122 is positioned in the vagina 26 so that a portion of the urinary tract is positioned between the first and second portion 126 and 128. A user can then place a magnetic source against their body. The magnetic source generates a field that causes the magnetic particles to vibrate. This vibrating action drives the agent from the caps 130 and 132, through the anterior vaginal wall 32, and into tissue proximal to the patient's urinary tract.

Figure 9:
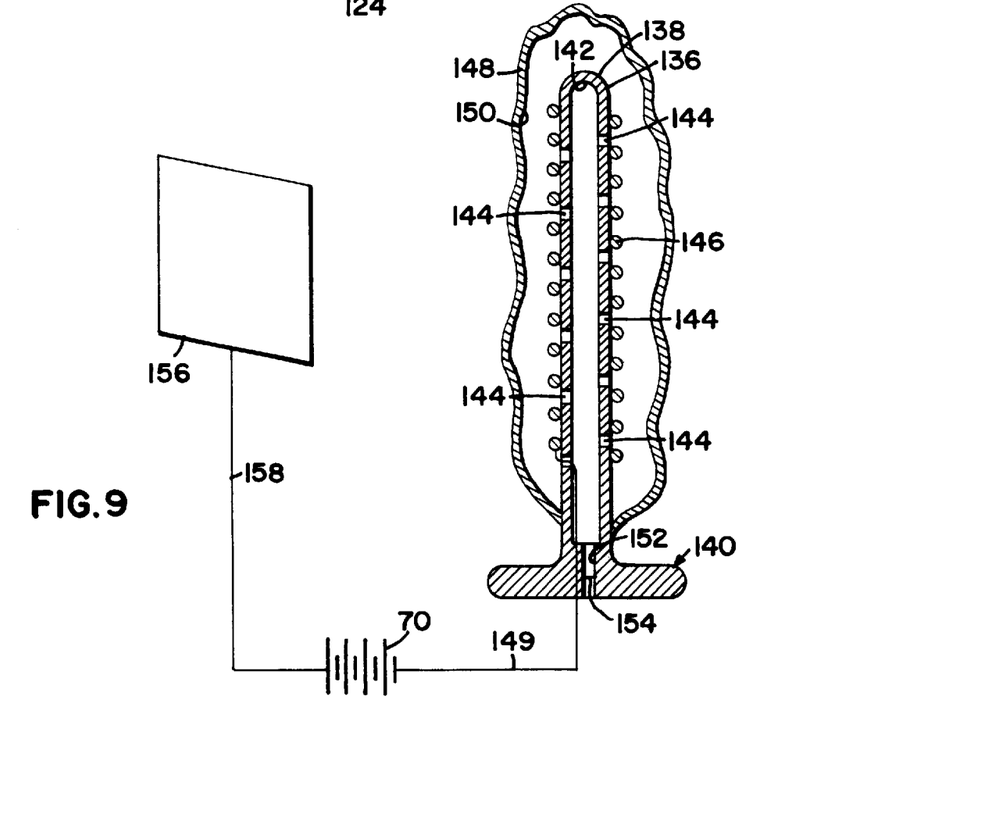
FIG. 9 shows a cross-section of an alternative embodiment of a vaginal insert useful for delivering an agent to the urogenital tract.

Referring to FIG. 9, another vaginal insert, generally shown as 134, has a base member 136 having a delivery portion 138 and a handle portion 140. The delivery portion 138 defines a chamber 142 and plurality of ports 144. A first electrode 146 is wound around the delivery portion 138. A first lead 149 extends from the first electrode 146 and through the handle portion 140 so that it may be connected to the power source 70.

A membrane 148 is operably connected to the base member 136 and defines a reservoir 150. The membrane 148 has a porous section for engaging the anterior vaginal wall 32. The ports 144 provide fluid communication between the chamber 142 and the reservoir 150. Additionally, the porous section of the membrane 148 can be located in only that portion of the membrane 148 that is placed against the anterior vaginal wall 32, thereby minimizing the amount of tissue outside of the urinary tract that is exposed to the agent. However, one skilled in this art will realize that the entire membrane 148 could be porous.

The handle portion 140 defines a supply port 152 that is covered by a septum 154, which seals if punctured by a needle. The supply port 152 provides a passage for supplying fluid into the chamber 142 and the reservoir 150. A second electrode 156 is a patch-type electrode and configured to be placed against the patient's body. The second electrode 156 has a second lead 158 for connecting to the power source 70.

In use, a patient or caregiver will inject a fluid containing an agent through the supply port 152 and fill the reservoir 150 and chamber 142. The fluid is supplied in an amount that fills the reservoir 150 with a pressure that permits the membrane 148 to remain pliable. The vaginal insert 134 is then placed in the vagina 26 so that the pores in the membrane 148 engage the anterior vaginal wall 32. The second electrode 156 is then placed against the patient's body at a position such as the patient's abdomen or thigh. The power supply 70 is activated so that an iontophoretic current passes between the first and second electrodes 146 and 156 and transports the agent from the reservoir 150 to tissues surrounding the urinary tract.

An advantage of vaginal insert 134 is that upon insertion, the vaginal walls will exert pressure against the membrane 148 and cause the fluid and agent to pass through the pores and through the anterior vaginal wall 32 where the agent can be absorbed by tissue surrounding the urinary tract.

Figure 10:
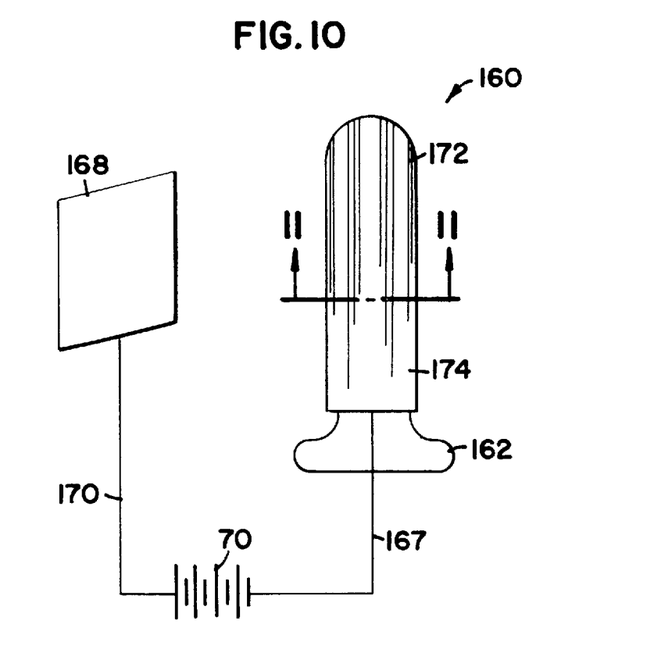
FIG. 10 shows an alternative embodiment of a vaginal insert useful for delivering an agent to the urogenital tract.
Figure 11A:
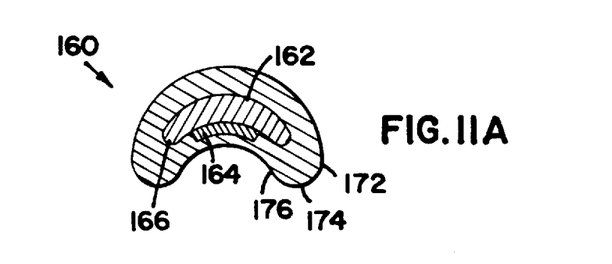
FIG. 11A shows a cross-section of the device shown in FIG. 10, the cross-section taken along line 11—11.

FIGS. 10 and 11A illustrate another vaginal insert, generally shown as 160, having a base member 162 and a first electrode 164 mounted on a surface 166 of the base member 162. The first electrode 164 is connected to the power source 70 via a first lead 167. A second, patch-type electrode 168 is configured to be placed against the skin and is attached to the power source 70 via a lead 170. An agent-retaining member 172 is operably connected to the base member 162 and has an outer surface 174. The base member 162 and agent-retaining member 172 are curved, thereby defining a channel 176 that is sized to engage the anterior vaginal wall 32 and receive tissue proximal the urethra 20. In this configuration, the agent-retaining member 172 can be formed from a material such as polymer matrix, hydrogel, or hydrophilic foam that can be impregnated with the agent. The agent-retaining member 172 is impregnated with an agent.

In use, the vaginal insert 160 is placed in the vagina 26 so that the curved outer surface 174 engages the anterior vaginal wall 32 and the channel 176 receives the tissue surrounding the urethra 20. The second electrode 168 is then placed against the patient's abdomen or thigh and the power source 70 is activated. The iontophoretic current passes between the first and second electrodes 164 and 168 and transports the agent from the agent-retaining member 172 to the tissue proximal to the urethra 20.

Figure 11B:
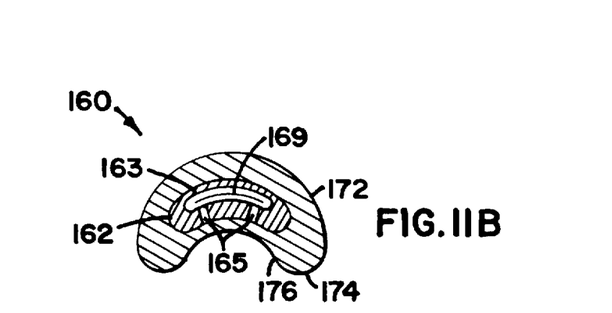
FIG. 11B shows a cross-section of an alternative embodiment of the device shown in FIG. 10, the cross-section taken along line 11—11.

In an alternative embodiment illustrated in FIG. 11B, the base member 162 can define a chamber 163 and a plurality of delivery ports 165. The delivery ports provide fluid communication between the chamber 163 and the surface of base member 162. An electrode 169 is positioned within the chamber 163. The electrode is operably connected to the first lead 167. The base member 162 also defines a hole (not shown) that is covered by a septum (not shown). In order to fill the chamber, the user can simply inject the agent or a solution containing the agent through the septum.

This alternative embodiment may contain the agent-retaining member 172. If the agent-retaining member 172 is used, it may contain a second therapeutic agent or a penetration enhancer. Alternatively, the agent-retaining member could be loaded only with water in order to provide a path for the iontophoretic current that passes between the electrodes 169 and 168. One skilled in the art will realize that the alternative embodiment shown in FIG. 11B is used in a substantially similar manner to the embodiment shown in FIG. 11A.

Figure 12:
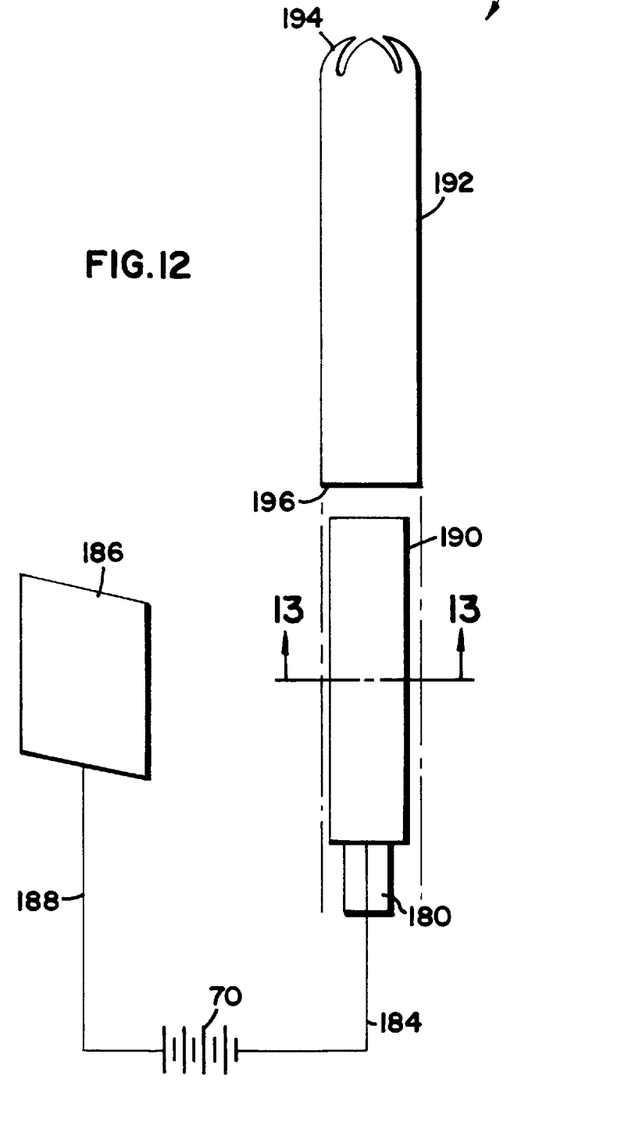
FIG. 12 shows an exploded view of an alternative embodiment of the vaginal insert useful for delivering an agent to the urogenital tract.
Figure 13:
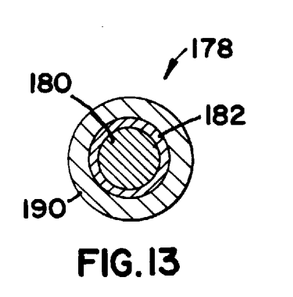
FIG. 13 shows a cross-section of the vaginal insert shown in FIG. 12, the cross-section taken along line 13—13.

Referring to FIGS. 12 and 13, another vaginal insert, generally shown as 178, has a base member 180 on which a first electrode 182 is mounted. The first electrode 182 is connected to a power source 70 via a first lead 184. A second, patch-type electrode 186 is configured to be placed against the patient's body at a point such as the abdomen or thigh. The second electrode 186 is then connected to the power source 70 via a second lead 188. A cotton-fiber matrix 190 is mounted on the base member. The cotton-fiber matrix 190 is absorbent and swells when it becomes wetted. One skilled in the art will realize that other materials that can be impregnated with an agent and that swells when wetted can be substituted for the cotton-fiber matrix 190.

The base member 180 and cotton-fiber matrix 190 are sized to fit within a tubular tampon-like applicator 192 when the cotton-fiber matrix 190 is not wetted. The tampon-like applicator 192 has a leading end 194 that is open and a trailing end 196 that is open.

In use, a user will position the base unit 180 and unwetted cotton-fiber matrix 190 in the tampon-like applicator 192 so that the first lead 184 extends through the trailing end 196. The cotton-fiber matrix 190 is then wetted with a fluid that contains an agent. The user uses the tampon-like applicator 192 to insert the base member 180 and cotton-fiber matrix 190 combination into the vagina 26 much like a tampon. During this process, the cotton-fiber matrix 190 expands as it is pushed out of the leading end 194 of the tampon-like applicator 192. After the tampon-like applicator 192 is removed from the vagina 26, the swelled cotton-fiber matrix 190 will conform to the contours of the interior vaginal wall. The second electrode 186 is placed against the patient's body at a point such as the abdomen or thigh. When an electric current passes between the first and second electrodes 182 and 186, the agent will be transported from the cotton-fiber matrix 190 to tissue surrounding the urinary tract, including the urethra 20.

One skilled in the art will realize that any of the embodiments described above can use alternative methods to transport the agent. For example, the active transport mechanism can be phonophoresis in which the electrodes are be replaced with an ultrasonic transducers. Phonophoresis uses ultrasonic waves to transport the agent from the vaginal insert to the target tissue that is proximal to the urinary tract. Another alternative transport mechanism is magnetophoresis. A magnetophoresis transport mechanism has both an agent and magnetic particles impregnated in an agent-retaining material that forms part of the vaginal insert. The magnetic particles will vibrate when subjected to an oscillating magnetic field, thereby driving the agent toward the target tissue. Additionally, all of the embodiments described above can be used with passive delivery, in which case electrodes, ultrasonic transducers, and magnetic particles are not necessary.

One skilled in the art will also realize that any agent-retaining material may be substituted for a polymer matrix, hydrogel, or foam. Additionally, the agent-retaining material can be a material that will dissolve or biodegrade when placed in a host environment, the vagina, thereby releasing the agent. A dissolvable, agent-retaining material can be used with either passive or active delivery.

Although the description of vaginal inserts and methods has been quite specific, it is contemplated that various modifications could be made. Accordingly, it is intended that the scope and spirit of the present invention can be dictated by the appended claims, rather than by the foregoing description.

The claimed invention is:

1. A vaginal insert for delivering an agent to a urogenital tract in a patient, the patient having a vagina, the vagina having an anterior wall, the vaginal insert comprising:

a base member sized to fit within the vagina;

an agent-retaining member operatively connected to the base member, the agent-retaining member having an outer surface, the outer surface defining a channel configured to engage the anterior vaginal wall and receive tissue proximal to the urethra.

2. The vaginal insert of claim 1 wherein the agent-retaining member is formed from a foam that is configured to be impregnated with the agent and to release the agent when engaging the anterior vaginal wall.

3. The vaginal insert of claim 2 further comprising:

a first electrode operably connected to the base member;

a second electrode operably configured to engage the patient's body; and a power supply operably connected to the first and second electrodes, the power supply configured to generate an electric current.

4. The vaginal insert of claim 2 wherein the agent-retaining member is a sheath formed from a polymer matrix, the sheath being configured to be impregnated with the agent.

5. The vaginal insert of claim 4 further comprising:

a first electrode operably connected to the base member;

a second electrode operably configured to engage the patient's body; and a power supply operably connected to the first and second electrodes, the power supply configured to generate an electric current.

6. The vaginal insert of claim 5 wherein the base member defines a chamber and a delivery port, the delivery port providing fluid communication between the polymer matrix and the chamber.

7. The vaginal insert of claim 6 wherein the first electrode is positioned within the chamber.

8. The vaginal insert of claim 6 wherein the first electrode is positioned between the base member and the sheath.

9. A vaginal insert for delivering an agent to a urogenital tract in a patient, the patient having a vagina, the vagina having an anterior wall, the vaginal insert comprising:

a member sized to fit within the vagina, the member having a surface defining a channel configured to engage the anterior vaginal wall and receive tissue proximal to the urethra, the member defining a chamber for retaining a supply of the agent and a plurality of ports, at least some of the ports being located along the channel, the plurality of ports being in fluid communication with the chamber; and first and second electrodes, the first electrode being operably connected to the member, the first and second electrodes configured to be operably connected to a power source so that an electrical current can pass between the first and second electrodes and through tissue proximal the urethra.

10. The vaginal insert of claim 9 wherein the second electrode is operably connected to the member thereby creating a bipolar configuration.

11. The vaginal insert of claim 10 wherein the power supply is positioned within the member.

12. The vaginal insert of claim 11 wherein the power supply is formed from an inductive circuit, the inductive circuit generating an electric current when subjected to a magnetic field.

13. The vaginal insert of claim 10 wherein the ports are covered by a polymer matrix.

14. The vaginal insert of claim 10 wherein at least one port is positioned on one side of the channel and at least one port is positioned on an opposite side of the channel.

15. A method of delivering an agent to a urogenital tract within a patient, the patient having a vagina, the vagina having an anterior wall, the method comprising the steps of:

inserting a vaginal insert into the vagina, the vaginal insert defining a channel and containing an agent, the channel being sized to engage the anterior vaginal wall and receive tissues proximal the urinary tract;

positioning tissue proximal to the urinary tract into the channel; and transporting the agent from the vaginal insert to tissue proximal the urinary tract.

16. The method of claim 15 wherein the vaginal insert includes a first electrode, the step of transporting including the steps of:

placing a second electrode in contact with the patient's body; and conducting a current between the first and second electrodes so that the current flows proximal to the urinary tract.

17. The method of claim 16 wherein the vaginal insert contains magnetic particles, the step of transporting the agent includes the step of vibrating the magnetic particles.

18. A vaginal insert for delivering an agent to a urogenital tract in a patient, the patient having a vagina, the vagina having an anterior wall, the vaginal insert comprising:

a reservoir member having an outer surface, the reservoir member being sized to be positioned in the vagina;

the outer surface of the reservoir member defining a channel, the channel configured to receive tissue proximal to the urethra when the reservoir is positioned in the vagina and the channel is facing the anterior vaginal wall.

19. The vaginal insert of claim 18 wherein the reservoir member includes a matrix configured to retain the agent.

20. The vaginal insert of claim 19 wherein the matrix is a polymer matrix.

21. The vaginal insert of claim 19 wherein the matrix is an open-cell foam.

22. The vaginal insert of claim 19 further comprising:

first and second electrodes, the first electrode operably connected to the reservoir member; and a power supply operably connected to the first and second electrodes, the power supply configured to generate an electric current.

* * * * *

UNITED STATES PATENT AND TRADEMARK OFFICE
CERTIFICATE OF CORRECTION

PATENT NO. : 5,816,248

DATED : OCTOBER 6, 1998

INVENTOR(S) : ANDERSON ET AL.

It is certified that error appears in the above-identified patent and that said Letters Patent is hereby corrected as shown below:

Title page, [54] Title: "TREATING UROGENITAL DISORDERS" should read ---DELIVERING AN AGENT---

Col. 1, Title, lines 2-3: "TREATING UROGENITAL DISORDERS" should read ---DELIVERING AN AGENT---

Signed and Sealed this

Twenty-third Day of May, 2000

Attest:

Q. TODD DICKINSON

*Attesting Officer*    *Director of Patents and Trademarks*